(12) United States Patent
Kemp et al.

(10) Patent No.: US 9,132,242 B2
(45) Date of Patent: Sep. 15, 2015

(54) AUTO-INJECTOR

(75) Inventors: Thomas Mark Kemp, Hertfordshire (GB); Timothy Donald Barrow-Williams, Hertfordshire (GB); Matthew Ekman, Cheshire (GB)

(73) Assignee: Sanofi-Aventis Deutschland GMBH, Frankfurt am Main ( * ) Notice: Subject to any disclaimer, the term of this patent is extended or adjusted under 35 U.S.C. 154(b) by 267 days.

(21) Appl. No.: 13/994,146

(22) PCT Filed: Dec. 21, 2011

(86) PCT No.: PCT/EP2011/073500
§ 371 (c)(1),
(2), (4) Date: Jun. 14, 2013

(87) PCT Pub. No.: WO2012/085019
PCT Pub. Date: Jun. 28, 2012

(65) Prior Publication Data
US 2013/0281935 A1    Oct. 24, 2013

(30) Foreign Application Priority Data
Dec. 21, 2010 (EP) .................... 10196065

(51) Int. Cl.
*A61M 5/32* (2006.01)
*A61M 5/20* (2006.01)
*A61M 5/315* (2006.01)

(52) U.S. Cl.
CPC .......... *A61M 5/3234* (2013.01); *A61M 5/2033* (2013.01); *A61M 5/3202* (2013.01); *A61M 5/326* (2013.01); *A61M 2005/206* (2013.01); *A61M 2005/208* (2013.01); *A61M 2005/3152* (2013.01); *A61M 2005/31516* (2013.01); *A61M 2005/3263* (2013.01)

(58) Field of Classification Search
CPC ..... A61M 5/20; A61M 5/2033; A61M 5/204; A61M 5/3232; A61M 5/3234; A61M 5/326; A61M 5/3257–5/3272; A61M 2005/2026; A61M 2005/206; A61M 2005/2013; A61M 2005/208; A61M 2005/3235; A61M 2005/3239
See application file for complete search history.

(56) References Cited

U.S. PATENT DOCUMENTS

| 2,605,766 A | 8/1952 | Uytenbogaart |
| 2002/0095120 A1 | 7/2002 | Larsen et al. |
| 2010/0280460 A1* | 11/2010 | Markussen .................. 604/195 |

FOREIGN PATENT DOCUMENTS

| WO | 0217996 A1 | 3/2002 |
| WO | 2009007305 A1 | 1/2009 |
| WO | 2009062508 A1 | 5/2009 |
| WO | 2009098502 A2 | 8/2009 |

* cited by examiner

*Primary Examiner* — Laura Bouchelle
(74) *Attorney, Agent, or Firm* — Fish & Richardson P.C.

(57) ABSTRACT

The invention refers to an auto-injector for administering a dose of a liquid medicament, comprising:
an outer casing, a syringe with a hollow needle and a stopper
a torsion spring and a gear arrangement for inserting the needle, delivering the medicament, and retracting the syringe after injection.
At least one skin contact trigger element is arranged at a proximal end of the outer case, the skin contact trigger element translatable in longitudinal direction between a proximal position and a distal position and biased in proximal direction in a manner to protrude from the outer casing in the proximal position, wherein in its proximal position the skin contact trigger element is arranged to prevent the spring means from being released and wherein the skin contact trigger element in its distal position is arranged to allow release of the spring means.

15 Claims, 16 Drawing Sheets

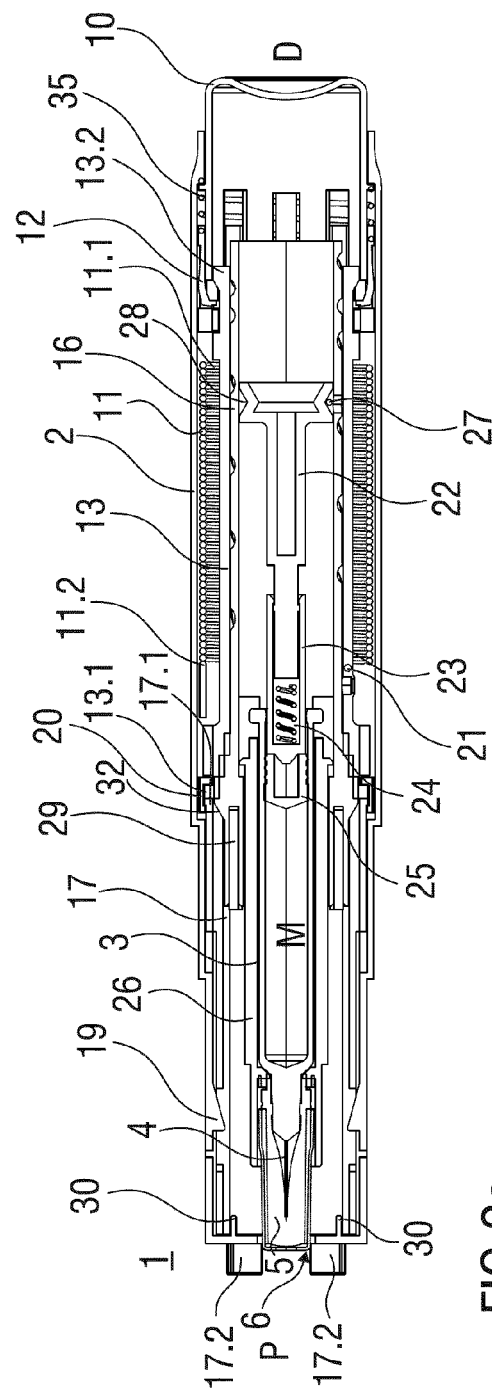
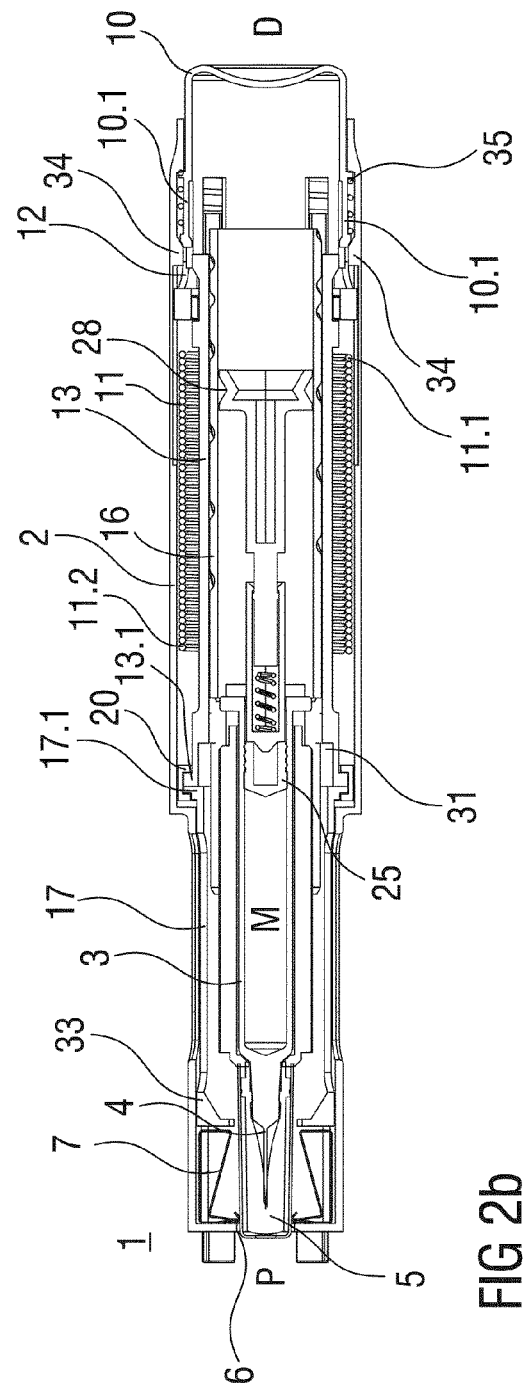
FIG 2a
FIG 2b

AUTO-INJECTOR

CROSS REFERENCE TO RELATED APPLICATIONS

The present application is a U.S. National Phase Application pursuant to 35 U.S.C. §371 of International Application No. PCT/EP2011/073500 filed Dec. 21, 2011, which claims priority to European Patent Application No. 10196065.6 filed Dec. 21, 2010. The entire disclosure contents of these applications are herewith incorporated by reference into the present application.

FIELD OF INVENTION

The invention relates to an auto-injector for administering a dose of a liquid medicament according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an under dose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

The post published EP 09174670.1 discloses an Auto-injector for administering a dose of a liquid medicament, comprising:

an elongate outer casing arranged to contain a syringe with a hollow needle and a stopper for sealing the syringe and displacing the medicament, the outer casing having a distal end and a proximal end with an orifice intended to be applied against an injection site, wherein the syringe is slidably arranged with respect to the outer casing, spring means capable of, upon activation:
pushing the needle from a covered position inside the outer casing into an advanced position through the orifice and past the proximal end,
operating the syringe to supply the dose of medicament, and
retracting the syringe with the needle into the covered position after delivering the medicament,
activating means arranged to lock the spring means in a pressurized state prior to manual operation and capable of, upon manual operation, releasing the spring means for injection. The spring means is a torsion spring grounded at one end in the outer casing and at the other end in a first gear member rotatable about a longitudinal axis, wherein the first gear member, upon rotation, is arranged for translatively moving a second gear member toward the proximal end, the second gear member prevented from rotating and coupled to the stopper in order to push it towards the proximal end, wherein the first gear member is engaged with the activating means prior to manual operation in a manner to prevent rotation and disengaged from the activating means upon manual operation.

SUMMARY

It is an object of the present invention to provide an improved auto-injector.

The object is achieved by an auto-injector according to claim 1.

Preferred embodiments of the invention are given in the dependent claims.

In the context of this specification the term proximal refers to the direction pointing towards the patient during an injection while the term distal refers to the opposite direction pointing away from the patient.

According to the invention, an auto-injector for administering a dose of a liquid medicament comprises:

an elongate outer casing arranged to contain a syringe with a hollow needle and a stopper for sealing the syringe and displacing the medicament, the outer casing having a distal end and a proximal end with an orifice intended to be applied against an injection site, wherein the syringe is slidably arranged with respect to the outer casing, spring means capable of, upon activation:
pushing the needle from a covered position inside the outer casing into an advanced position through the orifice and past the proximal end,
operating the syringe to supply the dose of medicament, and
retracting the syringe with the needle into the covered position after delivering the medicament, activating means arranged to lock the spring means in a pressurized state prior to manual operation and capable of, upon manual operation, releasing the spring means for injection.

The spring means is a torsion spring grounded at one end in the outer casing and at the other end in a first gear member rotatable about a longitudinal axis. The first gear member, upon rotation, is arranged for translatively moving a second gear member toward the proximal end, the second gear member prevented from rotating and arranged to be coupled to the stopper in order to push it towards the proximal end. The first gear member is engaged with the activating means prior to manual operation in a manner to prevent rotation and disengaged from the activating means upon manual operation.

The single torsion spring is used for inserting the needle, fully emptying the syringe and retracting the syringe and needle to a safe position after injection. A major advantage of the torsion spring with the gear arrangement is that force is exerted on the stopper and syringe in a smooth manner, whereas a conventional compression spring exhibits a rather abrupt force deployment which may spoil a glass syringe or other parts of the auto-injector.

According to the invention at least one skin contact trigger element is arranged at the proximal end of the outer case. The skin contact trigger element is translatable in longitudinal direction between a proximal position and a distal position and biased in proximal direction in a manner to protrude from the outer casing in the proximal position. When the skin contact trigger element is in its proximal position the spring means is prevented from being released. If the skin contact trigger element is in its distal position the spring means may be released.

In order to trigger an injection the auto-injector has to be pressed with its proximal end against an injection site, e.g. a patient's skin in a manner to translate the skin contact trigger element in distal direction into the housing. This motion may be used to directly trigger the auto-injector or preferably to unlock a trigger button. The probability for inadvertent operation of the auto-injector thus decreases due to the requirement of two user actions, pressing the auto-injector against the injection site and operating the trigger button.

The skin contact trigger element may be arranged on a proximal end of a retraction slider tube arranged to retract the syringe. The first gear member may be coupled to the refraction slider tube for joint translation but independent rotation. The refraction slider tube is arranged in a proximal part of the outer casing in a manner to be translatable in longitudinal direction but prevented from rotation, e.g. by one or more flats or splines guided in correspondent flats or splines in the outer casing. At least one latch for restricting axial translation of the retraction slider tube is provided in the outer casing in a manner to allow translation of the skin contact trigger element between the proximal and the distal position but prevent further translation of the retraction slider tube in distal direction. The latch is engaged for the most part of the operation of the auto-injector, i.e. before and during needle insertion and injection. When the second gear member is advanced into or near a maximum proximal position at the end of the injection the latches are disengaged by ramp features of the second gear member pushing the latches outward thus releasing the retraction slider tube for being translatively moved in distal direction. As long as the latches are engaged the second gear member is forced in proximal direction by the axially fixed and rotating first gear member. When the latches are disengaged the second gear member has at least nearly reached the end of its travel and bottomed out at the proximal end of the outer casing. Due to the disengaged latches the first gear member and the retraction slider tube are now pulled in distal direction by continued rotation of the torsion spring and the first gear member since the second gear member cannot advance further. The retraction slider tube comprises at least one dog feature for indirectly or directly engaging the syringe for retraction when the retraction slider tube is retracted by the first gear member. The syringe is retracted into the auto-injector until the hollow needle is fully covered. The dog feature preferably extends inwardly from the retraction slider tube through recesses in the second gear member.

The first and second gear members may be in the shape of tubes telescoped into each other. The first gear member may be a cam follower tube and the second gear member a lead screw tube, with the lead screw tube telescoped into the cam follower tube. The lead screw tube has a lead screw thread engaged with the cam follower tube by at least one ball bearing. The lead screw tube may have a multi start thread each of the threads engaged to the follower tube by a respective ball. In an alternative embodiment the cam follower tube may be engaged with the lead screw by a pin. However, the ball bearing is preferred in order to achieve a low friction contact.

For the purposes of clarity, from hereon in the following description of operation of the device, the first gear member will be referred to as the 'follower tube' and the second gear member will be referred to as the 'lead screw tube'.

The syringe may be held in an essentially tubular syringe carrier and supported at its proximal end therein, wherein the syringe carrier is slidably arranged in the lead screw tube. Supporting the syringe at its proximal end rather than at its flanges avoids damaging the syringe under load since the flanges are more fragile, in particular in a glass syringe. The dog feature is arranged for engaging the syringe carrier for retraction of the syringe.

The activating means may comprise a trigger button arranged at the distal end of the outer casing and operable by being pressed in proximal direction. The trigger button may be arranged to be prevented by the follower tube from being fully depressed when the skin contact trigger element is in its proximal position. The trigger button may be arranged to be unlocked for full depression by the follower tube when the skin contact trigger element is in its distal position.

At least one resilient beam element may be proximally arranged on the trigger button. A first rib is arranged in the outer case for deflecting the beam element inwards on depression of the trigger button by at least one ramp arranged on the first rib and/or on the beam element. A first shoulder is arranged on a distal end of the follower tube. The beam element is arranged to abut against the first shoulder when deflected and when the skin contact trigger element and hence the follower tube are in their proximal position. The first shoulder is arranged to be translated in distal direction by translation of the skin contact trigger element into the distal position in a manner to allow inward deflection of the beam element proximally behind the first shoulder.

A ring-shaped locking slider may be arranged inside the outer casing around the follower tube and in a splined engagement with the outer casing so as to allow translation and prevent rotation. The distal end of the torsion spring may be grounded in the outer case through this locking slider. In an initial state the locking slider is in a distal position splined to the follower tube so as to allow relative translation and prevent relative rotation thus statically resolving the load from the proximal end of the torsion spring through the follower tube and the locking slider to the distal end of the torsion spring. The locking slider is arranged to be translated in proximal direction by the trigger button on full depression in a manner to disengage from the splined connection to the follower tube so as to allow rotation of the follower tube.

In order to insert the hollow needle and to inject the dose the lead screw tube may be coupled to the stopper by a plunger which is releasably engageable with the lead screw tube for joint axial movement. The plunger is disengageable from the lead screw tube upon the lead screw tube reaching its maximum proximal position in order to allow the syringe to be retracted after injection.

The plunger may be engageable with the lead screw tube by at least one plunger ball detent. The ball detent may be held in a recess in the lead screw tube and engage a circumferential notch in the plunger. In order to stay engaged with the notch the ball is supported by the follower tube until the lead screw tube reaches the end of its travel. At this point the ball detent reaches a pocket in the follower tube so it is no longer supported and the detent ball drops into the pocket thus disengaging the plunger from the lead screw tube.

The plunger may comprise a plunger rear and a plunger front telescoped into each other. A plunger spring is arranged between the plunger rear and plunger front. The plunger spring may be a compression spring or a piece of resilient material such as foam, rubber, plastic or a pneumatic spring. It is arranged for being partially compressed when the plunger is advanced to push the stopper towards the proximal end. This partial compression happens due to friction between the stopper and the inner wall of the syringe and due to hydraulic resistance of the liquid medicament forced through the small fluid channel in the hollow needle.

The lead screw tube may be provided with pockets containing a viscous damper at the proximal end of the lead screw tube. The viscous damper is arranged for being compressed by a rib arranged in the proximal end of the outer casing when the lead screw tube nearly reaches its maximum proximal position. Thereby part of the load from the lead screw tube is resolved and the plunger spring is allowed to expand. Thus the stopper is advanced further by the compression spring or other resilient member so residual medicament is expelled from the syringe. This allows for dealing with the problem that the syringe and stopper are subject to large tolerances making it virtually impossible to expel the whole content of the syringe and trigger the retraction of the syringe exactly at the end of the injection. With conventional auto-injectors the stopper will either bottom out before the retraction can be triggered, (thus the syringe is emptied but the syringe and needle are never refracted so the risk for needlestick injuries is tremendously increased), or the retraction will be triggered before the stopper bottoms out in the syringe. In this case the syringe and needle are indeed retracted to a safe position but the syringe is not fully emptied.

The auto-injector with the viscous damper and the plunger spring allows for solving both problems, reliably retracting the hollow needle to a safe position and fully emptying the syringe which is particularly desirable with expensive drugs. Emptying the syringe is also important for dosage accuracy.

When the stopper has nearly reached the end of its travel the viscous damper contacts ribs in the proximal end of the outer casing. A velocity dependent load opposes the motion of the lead screw tube slowing it down. As a result load on the plunger is reduced, due to a reduced hydraulic resistance of the liquid medicament passing through the needle. This allows the plunger spring to expand and empty the residual dose of medicament. The lead screw tube is further advanced until it bottoms out in the proximal end of the outer casing. Shortly before this the ramp features disengage the latches so the refraction slider tube can be moved in the distal direction taking with it the syringe carrier and syringe as soon as the plunger and the lead screw tube are decoupled by the detent ball falling into the pocket. Thus the stopper is kept from stalling the retraction and the syringe is fully emptied.

The follower tube and the retraction slider tube may exhibit respective circumferential shoulders facing each other and held together by a coupling ring. This allows for independent rotation while joint axial movement is ensured.

In a preferred embodiment the lead screw thread has a variable pitch arranged in a manner to advance the lead screw tube faster and with less force when inserting the hollow needle (steep pitch) and more slowly with increased force when expelling the medicament (flat pitch). At the end of the travel of the lead screw tube the pitch is preferably even flatter in order to increase the force for compressing the viscous damper. A rapid needle insertion is known to reduce pain felt by the patient. A variable pitch also allows a steady delivery of the dose. The repeatability of the time required for the operational cycle of the auto-injector is important to the user. If the time required is highly variable between devices then the user may be confused and make errors in delivering the injection. Changing the pressure angle of the lead screw or cam track allows the load from the spring to be applied either more or less directly to the plunger, e.g. if there is a step in the device cycle that requires a high axial load such as when compressing the viscous damper or operating the latches for triggering the needle retraction.

Usually the hollow needle is equipped with a protective needle shield for keeping the needle sterile and preventing it from being mechanically damaged. The protective needle shield is attached to the needle when the auto-injector or the syringe is assembled.

In a preferred embodiment of the invention a finger guard is provided in the outer casing at the proximal end. The finger guard comprises a spring with two inwardly biased spring arms arranged for bearing against the protective needle shield. Furthermore the sheet metal spring has a respective locking arm assigned to each spring arm which is biased in distal direction and thus bearing against the respective spring arm when the protective needle shield is in place. The spring arms are arranged to move inwards when the protective needle shield is removed thus allowing the locking arms to move distally into a position where they prevent the spring arms from being pushed outward again.

The spring of the finger guard may be a sheet metal, wire or plastic spring.

Conventional auto-injectors achieve needle safety by starting with the needle held some distance back within the body of the device. Upon actuation the needle moves forward by a distance that is the sum of the hiding distance and the required injection depth. By using the aforementioned finger guard with the sheet metal spring the hiding distance may be safely reduced. Thus the auto-injector may be made shorter, more portable and attractive to users.

The housing may have at least one viewing window for inspecting the syringe.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
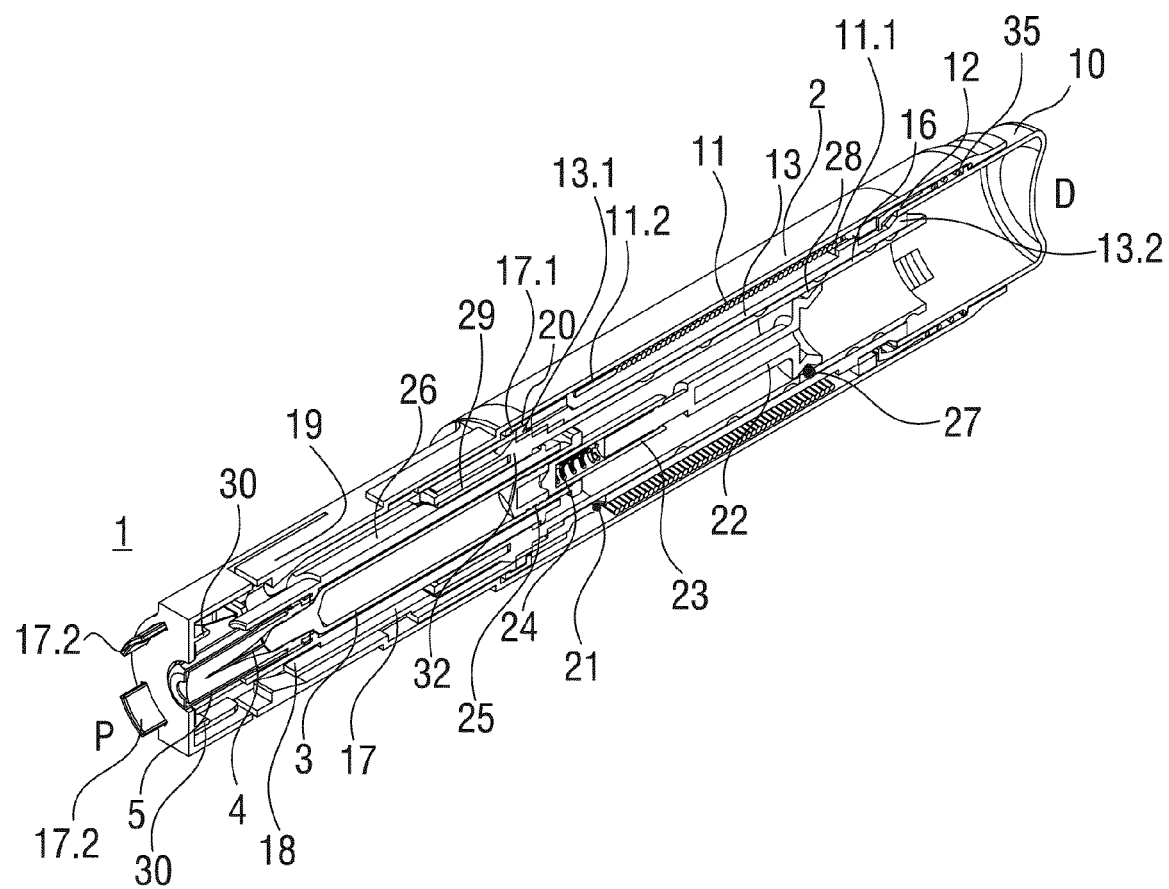
FIG. 1 is an isometric longitudinal section of the auto-injector in an initial state, FIG. 2 are two longitudinal sections if the auto-injector in different section planes.

FIGS. 1 and 2 show an auto-injector 1 in an initial state prior to an injection. FIGS. 2a and 2b are two longitudinal sections in different section planes of the auto-injector 1, the different section planes approximately 90° rotated to each other. The auto-injector comprises an elongate outer casing 2. A syringe 3 with a hollow needle 4 is arranged in a proximal part of the auto-injector 1. When the auto-injector 1 is assembled a protective needle shield 5 is attached to the needle 4 and protruding through an orifice 6 at the proximal end P. A finger guard 7 in the shape of a sheet metal spring is arranged near the protective needle shield 5. The finger guard 7 is shown in detail in FIGS. 4 and 5. The finger guard 7 comprises two spring arms 8 (cf. FIGS. 4 and 5) which are inwardly biased so they bear against the protective needle shield 5 as long as it is still in place. A respective locking arm 9 is assigned to each spring arm 8. The locking arms 9 are biased in distal direction D so they bear against a part of the spring arms 8 when the protective needle shield 5 is in place. As the protective needle shield 5 is pulled away from the needle 4 (see FIG. 5) the spring arms 8 move inwards and relax leaving a small gap between them just wide enough to let the needle 4 pass without touching it. This allows the locking arms 9 to come clear of the spring arms 8 and move distally into a position where they prevent the spring arms 8 from being pushed outward again so despite the rather big orifice 6 the user cannot touch the tip of the needle 4. The tips of the spring arms 8 where the spring arms 8 bear against the protective needle shield 5 are rounded off in order to facilitate removal of the protective needle shield 5.

In alternative embodiments the spring arms 8 and/or the locking arms 9 may be made of or comprise spring wire and/or plastic instead of sheet metal. The spring arms 8 and locking arms 9 may be integrally formed as illustrated. They may also be separate parts, e.g. attached to inner walls of the proximal part of the auto-injector 1.

Figure 4:
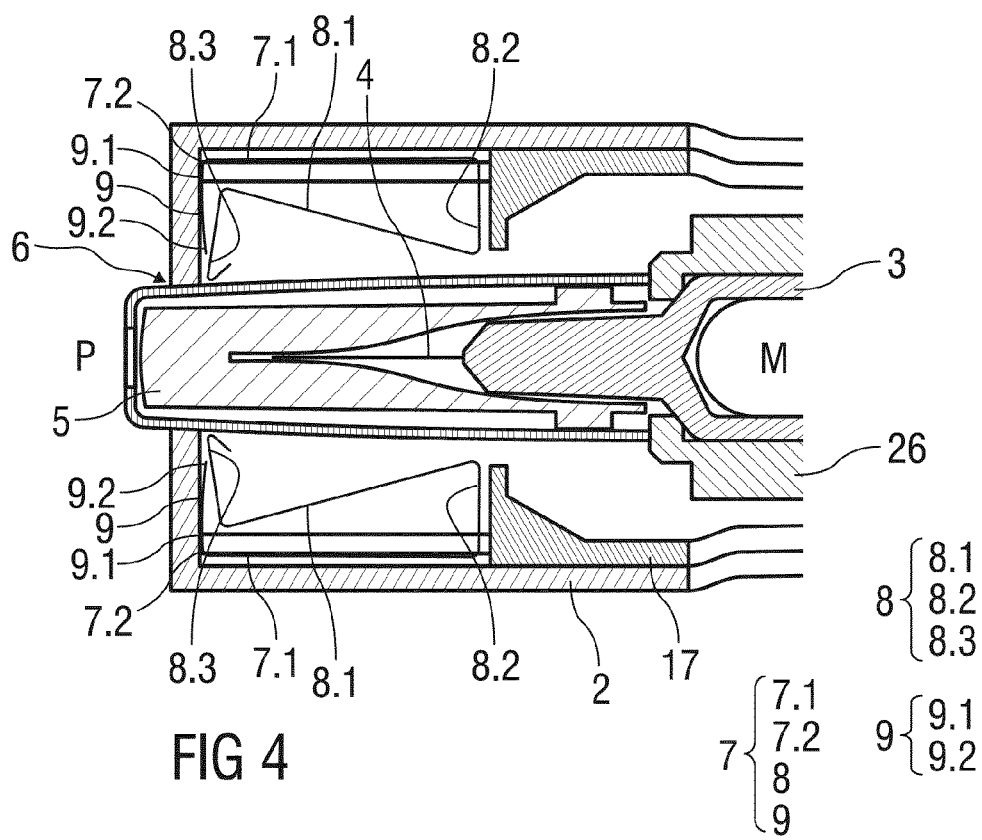
FIG. 4 is a detail view of a finger guard prior to use.
Figure 5:
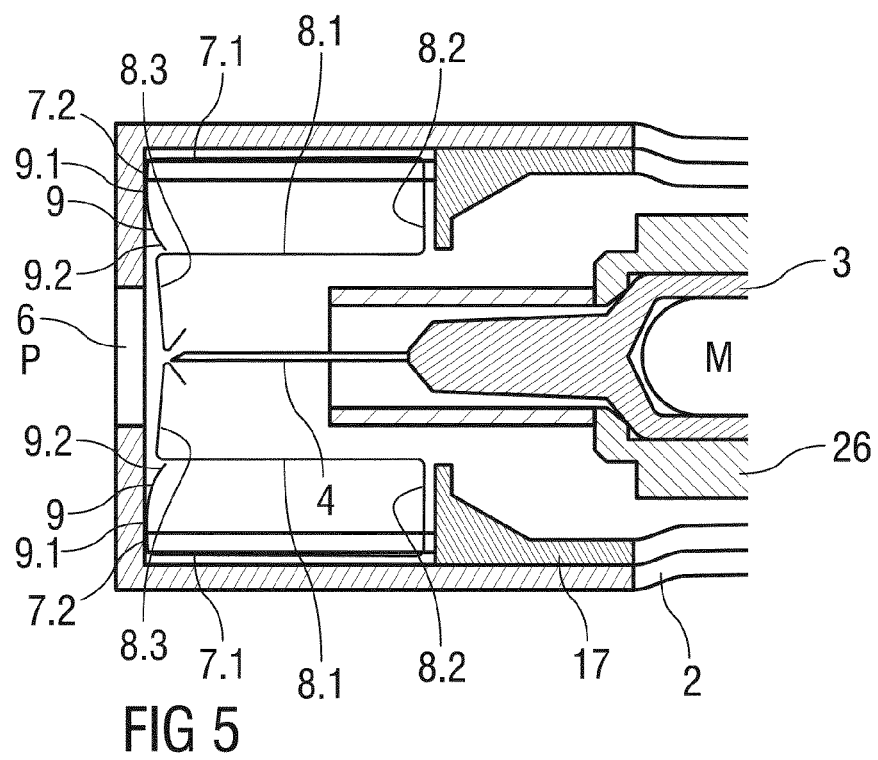
FIG. 5 is a detail view of the finger guard after removal of a rigid needle shield.

Referring now to FIGS. 4 and 5, the spring arms 8 are essentially S-shaped with a longitudinal leg 8.1 in the middle and two transversal legs 8.2, 8.3 adjoining the longitudinal leg 8.1. When the spring arm 8 is relaxed, the transversal legs 8.2, 8.3 are essentially parallel to each other. An outer transversal leg 8.2 of each spring arm 8 adjoins a wall portion 7.1 of the sheet metal spring 7. The other, inner transversal 8.3 leg of each spring arm 8 is intended to bear against the protective needle shield 5. When the protective needle shield 5 is removed, a small gap is defined between the two inner transversal legs 8.3 of the spring arms 8. The locking arm 9 is a short arm with an outer end 9.1 adjoining a front portion 7.2 of the sheet metal spring 7 and with an inner end 9.2 bearing against the inner transversal leg 8.3 in distal direction D when the protective needle shield 5 is in place. When the protective needle shield 5 is removed the spring arms 8 move together and the locking arms 9 come clear of the inner transversal leg 8.3 when the joint between the inner transversal leg 8.3 and the longitudinal leg 8.1 passes the inner end 9.2. The inner end 9.2 locks behind the longitudinal leg 8.1 thus preventing the spring arm 8 from being pushed outward again. The tips of the spring arms' 8 inner transversal legs 8.3 where the spring arms 8 bear against the protective needle shield 5 are rounded off in order to facilitate removal of the protective needle shield 5.

At the distal end D of the auto-injector 1 a trigger button 10 for releasing a torsion spring 11 is arranged.

Figure 3:
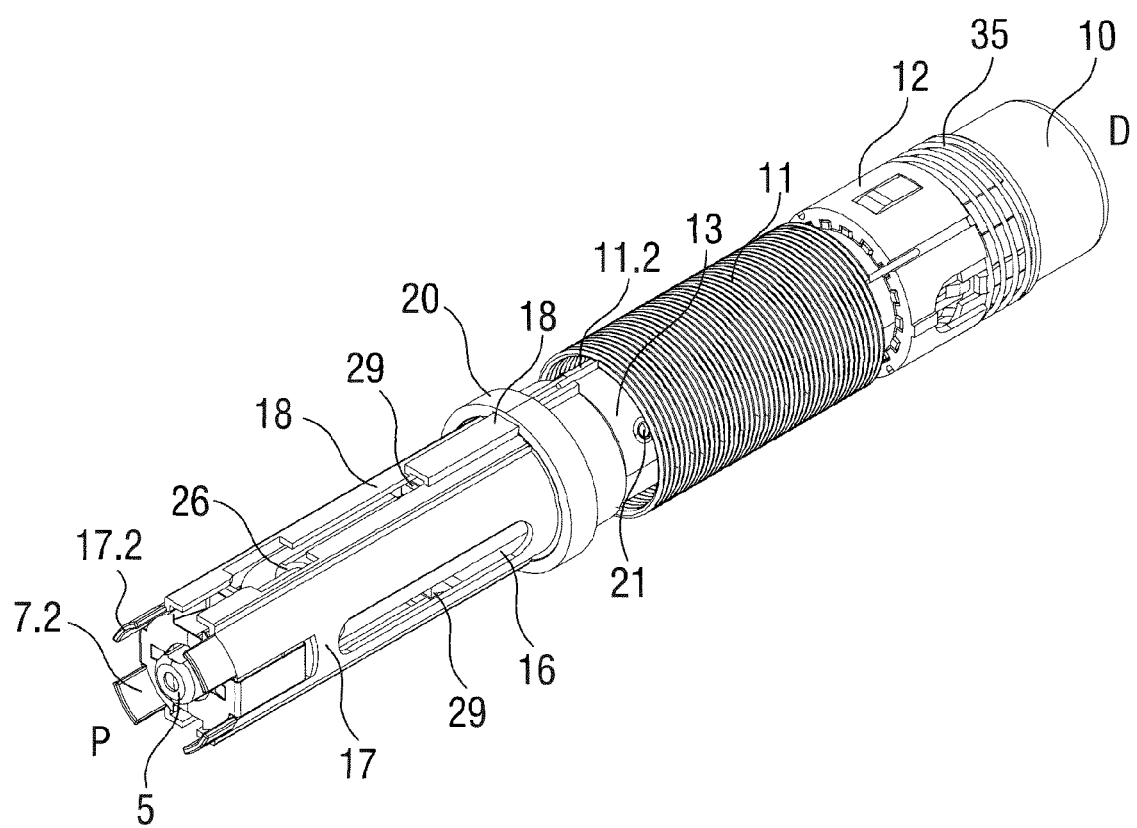
FIG. 3 is an isometric view of the internals of the auto-injector without the housing.

The torsion spring 11 is arranged inside the outer casing 2 and grounded with its distal end 11.1 in a ring-shaped locking slider 12 arranged in the outer casing 2 near the distal end D of the auto-injector 1. The proximal end 11.2 of the torsion spring 11 is grounded in a follower tube 13 arranged inside the torsion spring 11 and rotatable with respect to the outer casing 2. In the initial state the locking slider 12 is in a splined engagement with the follower tube 13 preventing rotation of the follower tube 13 relative to the locking slider 12 and hence preventing release of the torsion spring 11 (see FIG. 3). The locking slider 12 is arranged to be translated in the proximal direction P by the trigger button 10 for disengaging its splined engagement to the follower tube 13 but is splined into the outer case 2 to statically resolve any torque from the torsion spring 11.

Figure 6:
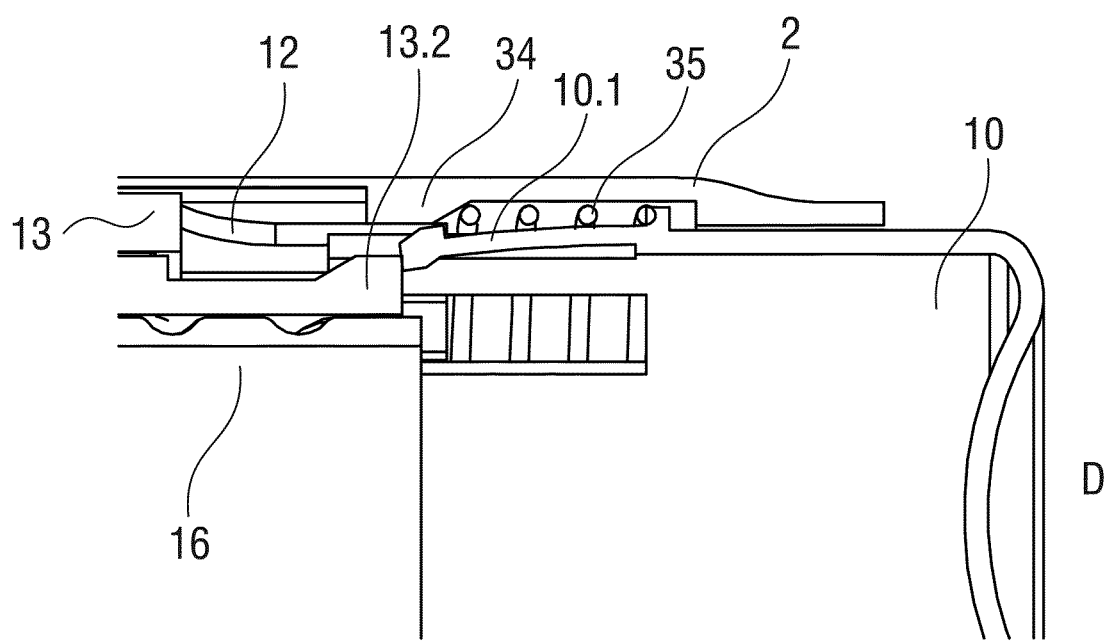
FIG. 6 is a detail view of a trigger button prevented from being depressed by an interlock.
Figure 9:
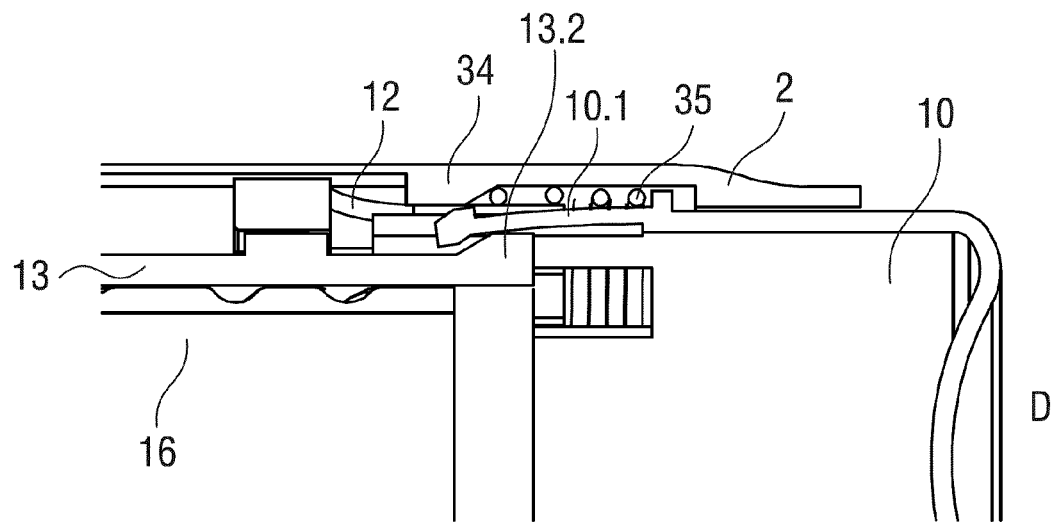
FIG. 9 is a detail view with the released interlock and the depressed trigger button.
Figure 10:
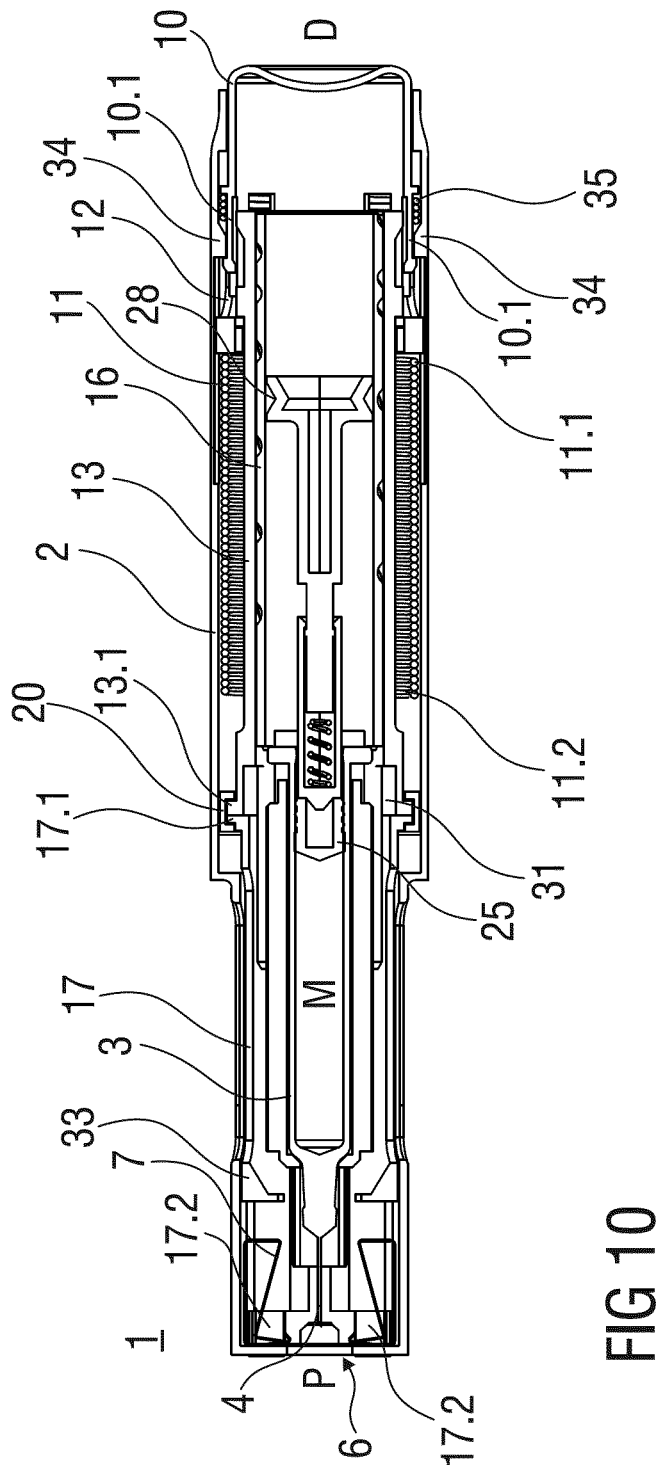
FIG. 10 is a longitudinal section of the auto-injector with the trigger button fully depressed.

In the initial state, full depression of the trigger button 10 is prevented by a skin interlock mechanism described below. If the trigger button 10 is depressed, a beam element 10.1 on the trigger button 10 is forced to deflect inwards through ramped interference with a first rib 34 in the outer case 2. When deflected, the beam element 10.1 is located such that it interferes with a first shoulder 13.2 on the distal end of the follower tube 13 preventing further depression of the trigger button 10 and thus initiation of the auto-injector 1 (see FIG. 6). The skin interlock is arranged to change the position of the follower tube 13 such that the first shoulder 13.2 is located distally from the beam element 10.1 so the beam element 10.1 no longer interferes with the follower tube 13. Hence the trigger button 10 can be fully depressed for starting an injection cycle. (See FIG. 9)

The follower tube 13 is telescoped with a lead screw tube 16. The lead screw tube 16 is supported and guided in a retraction slider tube 17 arranged in the proximal part of the outer casing 2 in a manner to prevent the lead screw tube 16 from rotating while allowing it to be moved axially in proximal direction P. The retraction slider tube 17 in turn is engaged with the outer casing 2 by flats 18 (cf. FIG. 2 and latches 19 in a manner to prevent both rotation and translation with respect to the outer casing 2 at least in the initial situation shown in FIGS. 1 and 2. It will be shown in the following how the retraction slider tube 17 is disengaged from the latches 19 for being axially moved. The retraction slider tube 17 and the follower tube 13 are provided with respective second and third shoulders 17.1, 13.1 held together by a coupling ring 20 for allowing relative rotation but preventing them from being independently axially moved. The lead screw tube 16 has an external lead screw which is engaged with the follower tube 13 by one or more ball bearings 21. Rotation of the follower tube 13 therefore results in translative movement of the lead screw tube 16.

In the initial situation shown in FIGS. 1 and 2 the retraction slider tube 17 cannot rotate but move axially in the distal direction D, the follower tube 13 is prevented from rotating by the spline engagement with the locking slider 12 and the lead screw tube 16 is prevented from rotation by its engagement with refraction slider tube 17.

A number of skin contact elements 17.2 arranged proximally on the retraction slider tube 17 protrude through recesses in the proximal end of the outer case 2.

A sequence of operation of the auto-injector 1 is as follows:

The user removes the protective needle shield 5 from the needle 4. For this purpose a device cap (not shown) may be attached to the protective needle shield 5. When the protective needle shield 5 is removed the finger guard 7 locks into place to protect the user from accidental needle-stick injuries.

Figure 7:
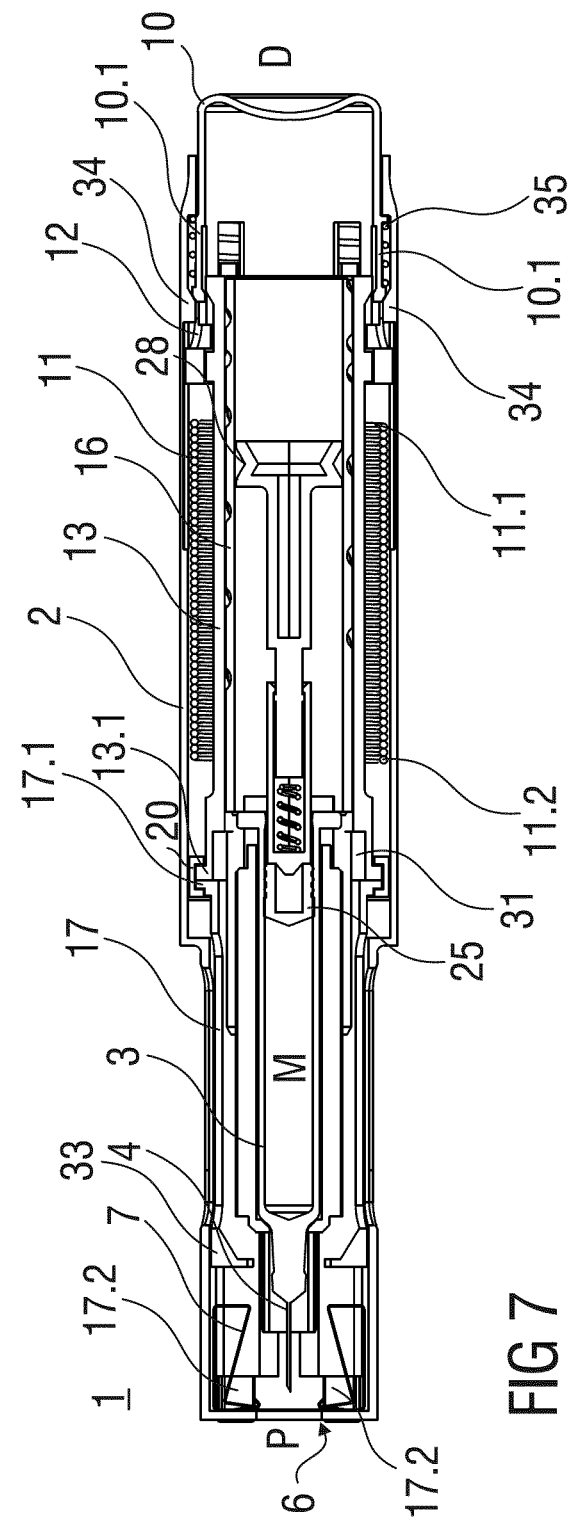
FIG. 7 is a longitudinal section of the auto-injector with the interlock released.
Figure 8:
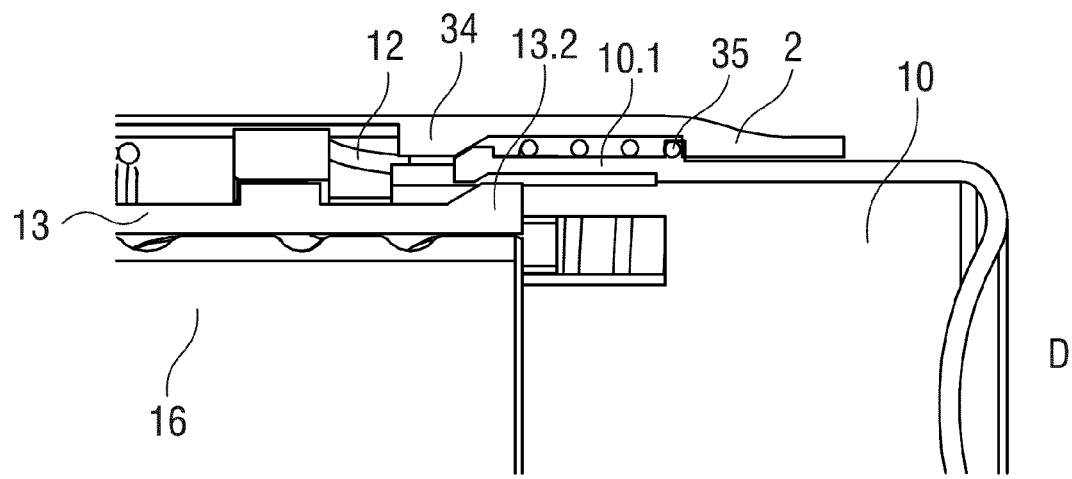
FIG. 8 is a detail view with the released interlock prior to depression of the trigger button.

When ready to do so, the user pushes the auto-injector 1 against the injection site. The user presses the proximal end P of the auto-injector 1 against the injection site. This causes the skin contact elements 17.2 of the retraction slider tube 17 to be depressed inside the outer casing 2 (see FIG. 7). The follower tube 13 is axially fixed to the retraction slider tube 17 through the coupling ring 20 and thus the whole assembly of the refraction slider tube 17 and the follower tube 13 translate within the outer casing 2 in the distal direction D with depression of the skin contact element 17.2. This motion is opposed by a button spring 35. Once translated, the first shoulder 13.2 on the follower tube 13 no longer interferes with the beam element 10.1 on the trigger button 10. The beam element 10.1 may deflect inwards proximally behind the first shoulder 13.2. Hence, the trigger button 10 can now be fully depressed.

The button spring 35 may be arranged as a metal compression spring as illustrated, but it could equally be embodied as an integrally moulded flexible beam feature on either the trigger button 10 or the locking slider 12.

When the trigger button 10 is depressed it comes into contact with the locking slider 12 translating it in proximal direction P when fully depressed. With axial movement of the locking slider 12 its splined coupling with the follower tube 13 is disengaged so load from the proximal end of the torsion spring 11 is no longer statically resolved. The torque from the torsion spring 11 is released causing the follower tube 13 to rotate and drive the lead screw tube 16 forward.

Figure 11:
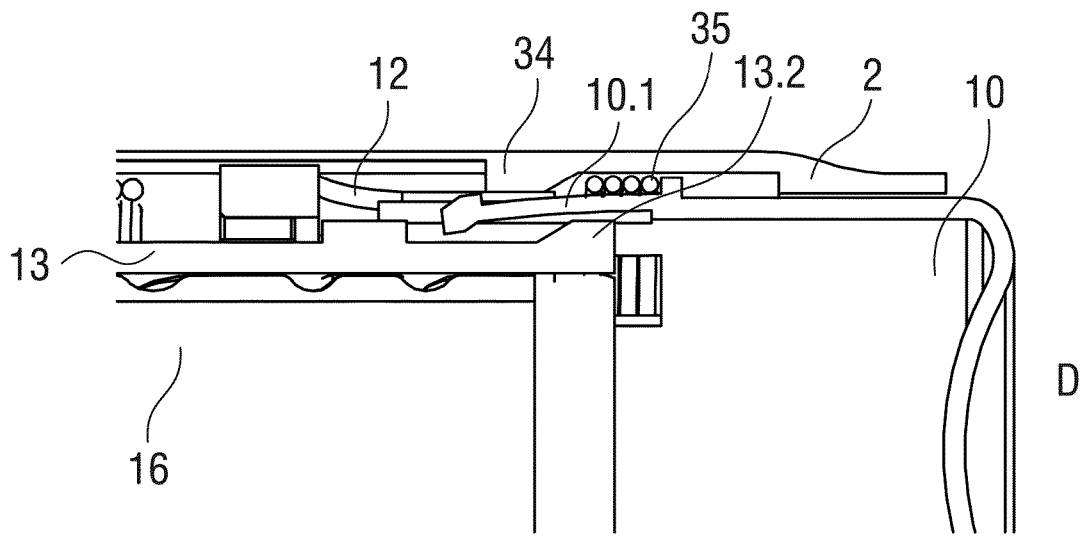
FIG. 11 is a detail view with the trigger button almost fully depressed.
Figure 12:
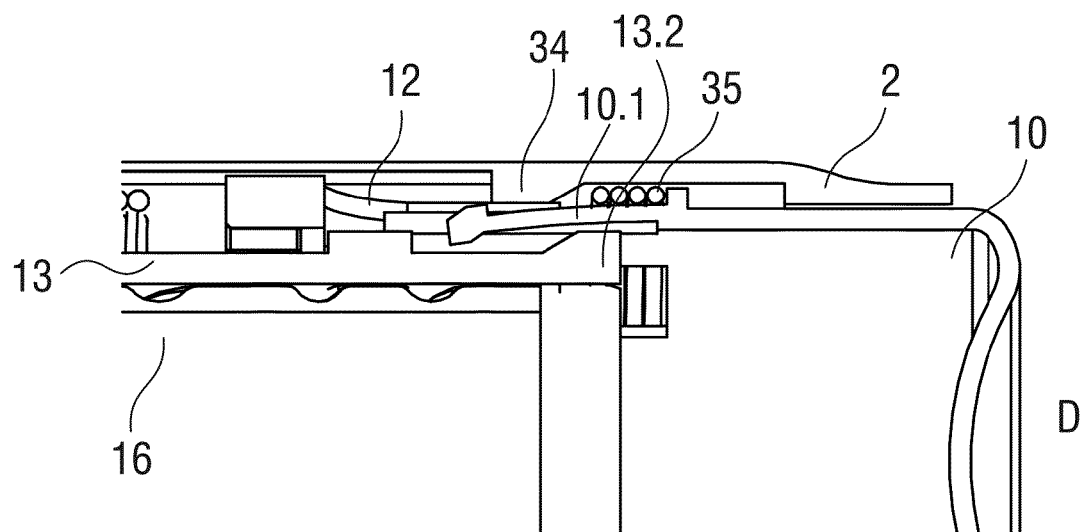
FIG. 12 is a detail view with the trigger button fully depressed and latched to the housing.
Figure 13:
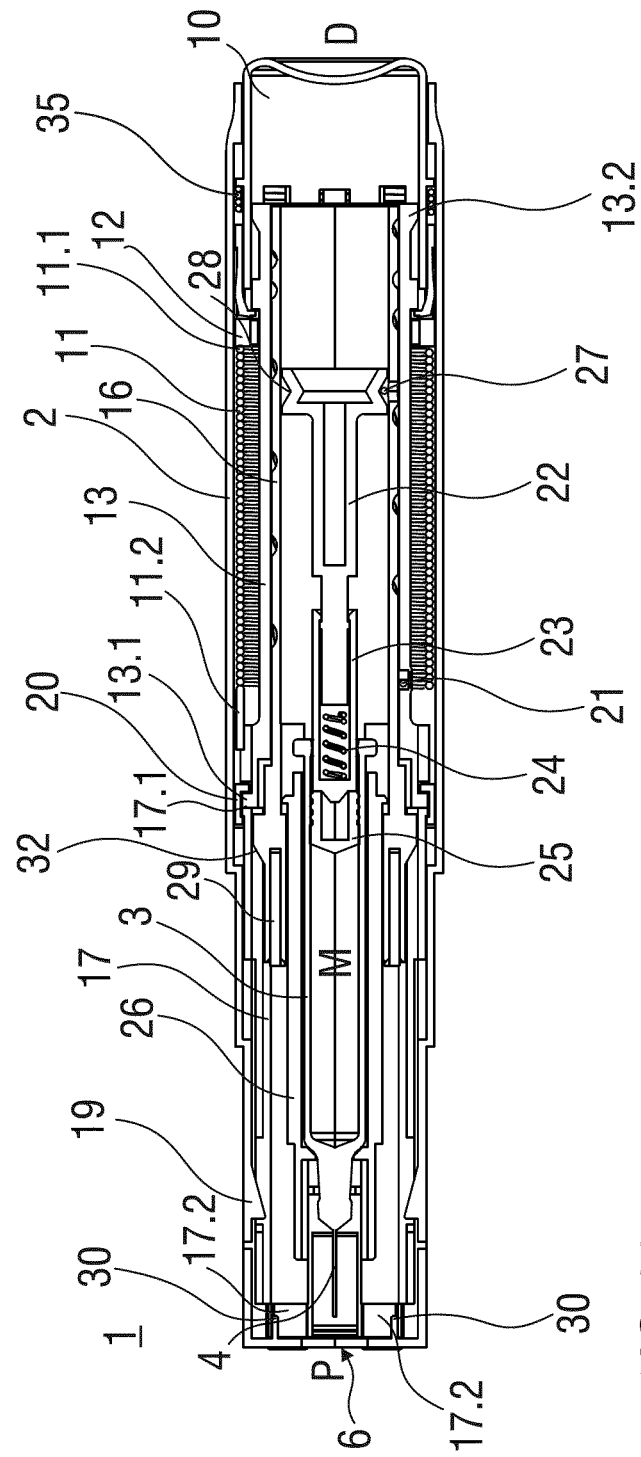
FIG. 13 is a longitudinal section of the auto-injector in the other section plane with the trigger button fully depressed.

When the trigger button 10 is fully depressed the resilient beam element 10.1 flexes outward again behind the first rib 34 thus locking the trigger button 10 in this depressed position. (See FIG. 11). This could likewise be achieved by a separate locking feature.

The rotation of the follower tube 13 causes translative movement of the lead screw tube 16 in proximal direction P. Inside the lead screw tube 16 a two part plunger with a plunger rear 22 and a plunger front 23 is arranged, the plunger rear 22 telescoped into the hollow plunger front 23. In the plunger front 23 a plunger spring 24 in the shape of a compression spring is arranged which bears against the plunger rear 22 when the plunger rear 22 pushed in proximal direction P. The plunger front 23 in turn pushes against a stopper 25 arranged for sealing the syringe 3 distally and for displacing a liquid medicament M through the hollow needle 4. The syringe 3 is held in a tubular syringe carrier 26 and supported at its proximal end therein. The plunger rear 22 is coupled for joined axial movement to the lead screw tube 16 by a plunger ball 27 arranged in a recess in the lead screw tube 16 and guided in a circumferential notch 28 of the plunger rear 22. In the initial position shown in FIGS. 1 and 2, the plunger ball 27 is held in position by the follower tube 13 in order to keep the plunger rear 22 and lead screw tube 16 from disengaging.

Consequently, when the lead screw tube 16 is advanced in proximal direction P the syringe 3 is driven forward by the plunger pushing on the stopper 25.

The external lead screw of the lead screw tube 16 has a variable pitch. In the embodiment shown in the figures the pitch is steeper in the proximal part of the external lead screw. This allows for a rapid insertion of the hollow needle 4 into the patient's skin in order to avoid unnecessary pain for the patient. The load required to insert a siliconized fine gauge needle is thought to be in the region of 5 N, which is relatively low so a steep screw pitch can be used with little risk of the screw engagement locking FIG. 14 shows the auto-injector 1 with the hollow needle 4 fully advanced.

In case the screw engagement between the follower tube 13 and the lead screw tube 16 comprises more than one ball bearing 21 each ball 21 may be engaged with a respective screw thread so the lead screw tube 16 would have a multi-start thread.

Figure 14:
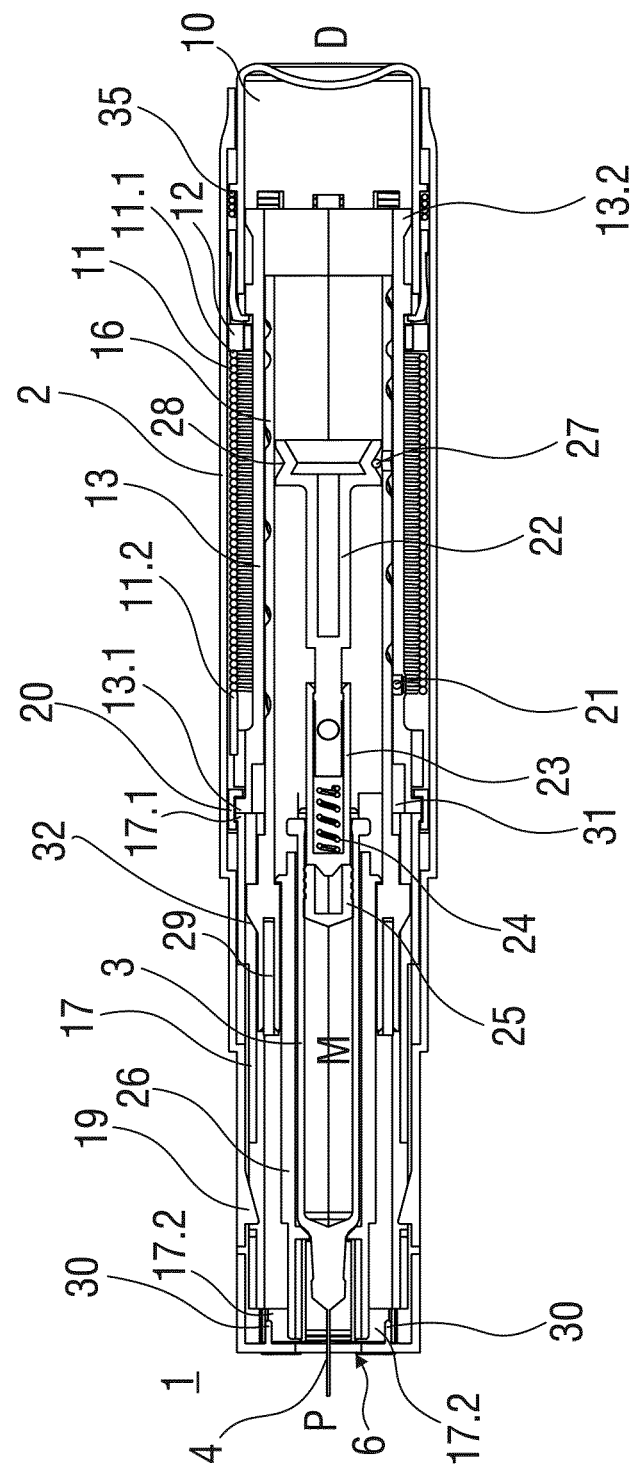
FIG. 14 is a longitudinal section of the auto-injector with an injection needle advanced for insertion into an injection site.

In FIG. 14 the syringe carrier 26 has bottomed out at the proximal end P of the outer casing 2 thus defining an injection depth, e.g. for a subcutaneous injection.

Figure 15:
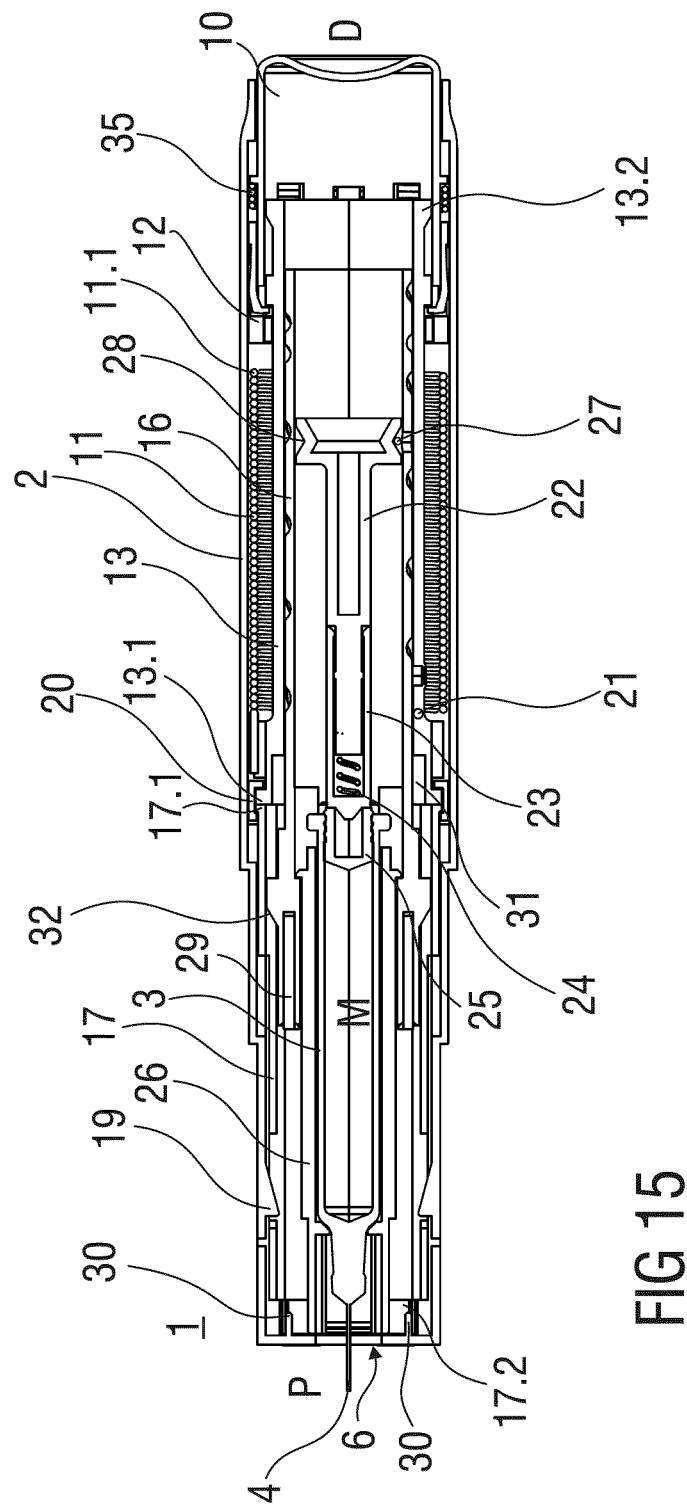
FIG. 15 is a longitudinal section of the auto-injector during compression of a plunger spring.
Figure 16:
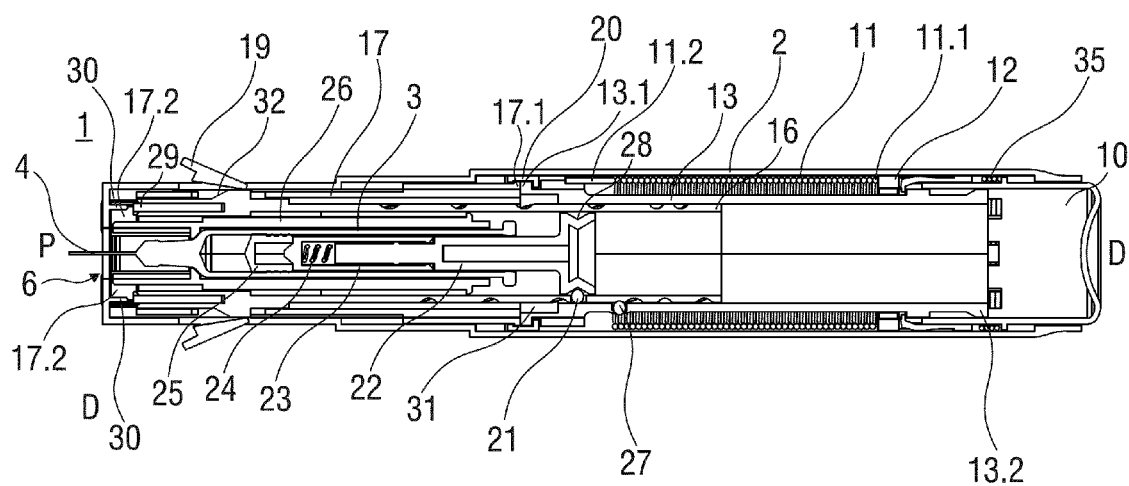
FIG. 16 is a longitudinal section of the auto-injector during injection of a medicament stored in a syringe.

As the torsion spring 11 continues rotating the lead screw tube 16, and plunger rear 22 are further forwarded. Due to friction effective between the stopper 25 and the inner wall of the syringe 3 and due to the thin fluid channel inside the hollow needle 4 opposing the displacement of the medicament M the stopper 25 exerts a load against the forward movement of the plunger front 23. Thus, the plunger spring 24 is slightly compressed (see FIG. 15). The thrust load is reacted through the coupling ring 20 into the retraction slider tube 17 which is coupled to the outer casing 2 by the latches 19. Thus the follower tube 13 is kept from moving further in distal direction D. With continued forward movement of the plunger the stopper 25 is advanced and injects the medicament M from the syringe 3 into the injection site (see FIG.

16). During injection of the dose of medicament M the pitch of the lead screw is slightly reduced compared to the needle insertion in order to give a greater mechanical advantage to the lead screw engagement and avoid it stalling due to the increased load.

Figure 17:
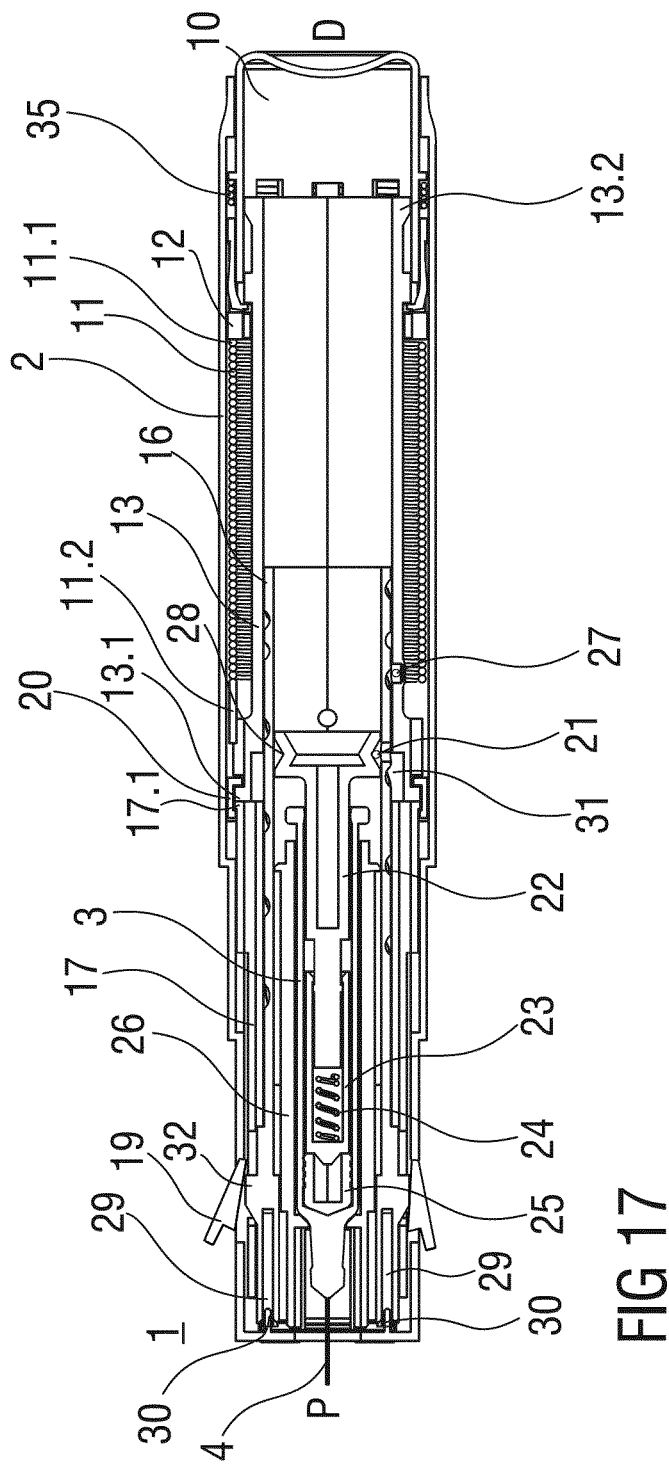
FIG. 17 is a longitudinal section of the auto-injector during expansion of the plunger spring for emptying a residual dose of the medicament.

In FIG. 17 the auto-injector 1 is shown towards the end of the dose, i.e. just before the stopper 25 bottoms out in the syringe 3. In this situation viscous dampers 29 contained in pockets in the proximal end of the lead screw tube 16 contact small second ribs 30 in the proximal end P of the outer casing 2. Thus load from the torsion spring 11 is shared between the stopper 25 and the contact between the second ribs 30 and the viscous dampers 29, so the plunger spring 24 is allowed to extend and complete the dose by fully advancing the stopper 25. This allows for fully emptying the syringe 3 before starting to retract the needle 4.

The viscous damper 29 has a speed dependent load characteristic. In this instance the load from the torsion spring 11 is almost constant over the small axial travel of the viscous damper 29 so the speed can be tuned so that the plunger spring 24 has enough time to fully expel the residual contents of the syringe 3. The material of the viscous damper 29 may be viscoelastic foam or a fluid forced through a small orifice.

A change in the lead screw pitch at this point allows a controlled increase in the mechanical advantage to apply sufficient force to the mechanism.

Figure 18:
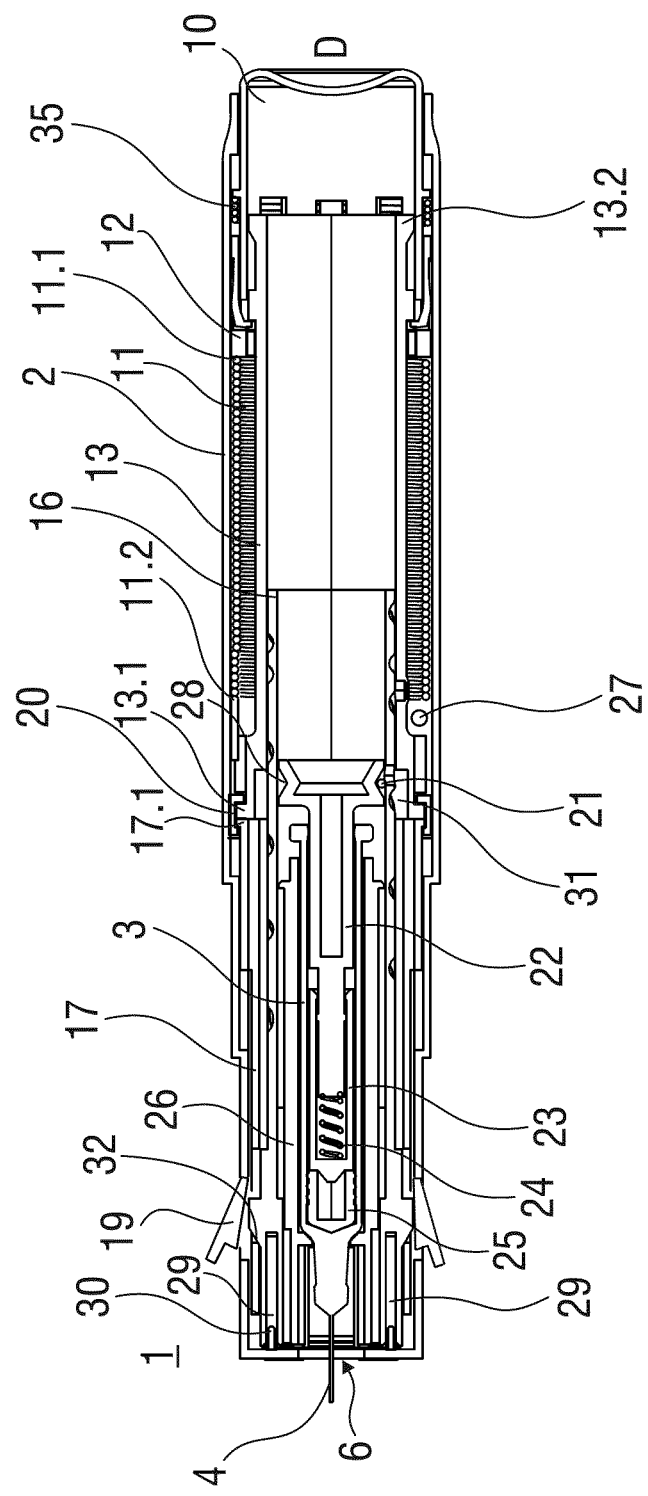
FIG. 18 is a longitudinal section of the auto-injector at the end of dose.
Figure 19:
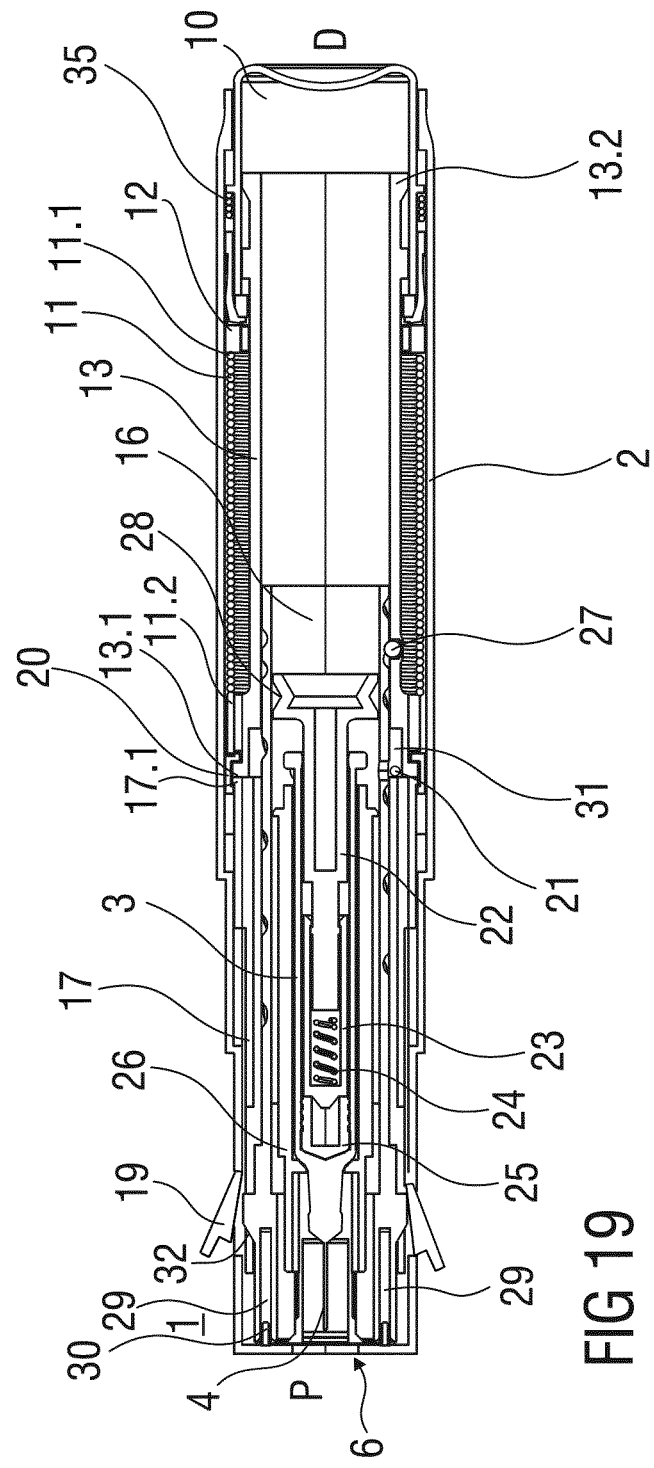
FIG. 19 is a longitudinal section of the auto-injector with the needle retracted after injection.

In FIG. 18 the stopper 25 has bottomed out in the syringe 3 and the lead screw tube 16 reaches the end of travel. The plunger ball 27 disengages the plunger rear 22 from the lead screw tube 16 by dropping out of its recess into a pocket 31 in the follower tube 13. Just after this the latches 19 are released by ramp features 32 of the lead screw tube 16 pushing them outward so the retraction slider tube 17 and the follower tube 13 are released from the outer casing 2 for translation. Since the lead screw tube 16 has bottomed out at the proximal end P of the outer casing continued rotation of the torsion spring results in a backward movement of the retraction slider tube 17 and the follower tube 13 which is still rotating. The retraction slider tube 17 takes along the syringe carrier 26 and syringe 3 with the needle 4 and retracts them into the auto-injector 1 until the needle 4 is fully covered (See FIG. 19). For this purpose the retraction slider tube 17 has one or more dog features 33 (see FIG. 2) extending inwardly through recesses in the lead screw tube 16 and engaging the syringe carrier 26.

The auto-injector 1 may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

The invention claimed is:

1. Auto-injector for administering a dose of a liquid medicament, comprising:
    an elongate outer casing arranged to contain a syringe with a hollow needle and a stopper for sealing the syringe and displacing the medicament, the outer casing having a distal end and a proximal end with an orifice intended to be applied against an injection site, wherein the syringe is slidably arranged with respect to the outer casing,
    spring means capable of, upon activation:
    pushing the needle from a covered position inside the outer casing into an advanced position through the orifice and past the proximal end,
    operating the syringe to supply the dose of medicament, and
    retracting the syringe with the needle into the covered position after delivering the medicament,
    activating means arranged to lock the spring means in a pressurized state prior to manual operation and capable of, upon manual operation, releasing the spring means for injection,
    wherein the spring means is a torsion spring grounded at one end in the outer casing and at the other end in a first gear member rotatable about a longitudinal axis, wherein the first gear member, upon rotation, is arranged for translatively moving a second gear member toward the proximal end, the second gear member prevented from rotating and arranged to be coupled to the stopper in order to push it towards the proximal end, wherein the first gear member is engaged with the activating means prior to manual operation in a manner to prevent rotation and disengaged from the activating means upon manual operation,
    characterized in that at least one skin contact trigger element is arranged at the proximal end of the outer case, the skin contact trigger element translatable in longitudinal direction between a proximal position and a distal position and biased in proximal direction in a manner to protrude from the outer casing in the proximal position, wherein in its proximal position the skin contact trigger element is arranged to prevent the spring means from being released and wherein the skin contact trigger element in its distal position is arranged to allow release of the spring means.

2. Auto-injector according to claim 1, characterized in that the skin contact trigger element is arranged on a proximal end of a retraction slider tube, wherein the retraction slider tube is arranged in a proximal part of the outer casing in a manner to be prevented from rotation and wherein at least one latch for restricting axial translation of the retraction slider tube is provided in the outer casing, the latch being disengageable by at least one ramp feature on the second gear member when the second gear member is in or near a maximum proximal position, wherein the retraction slider tube comprises at least one dog feature for retracting the syringe when the retraction slider tube is retracted by the first gear member.

3. Auto-injector according to claim 1, characterized in that the first gear member is a cam follower tube and that the second gear member is a lead screw tube, wherein the lead screw tube is telescoped in the cam follower tube, wherein the lead screw tube has a lead screw thread engaged with the cam follower tube by at least one ball bearing.

4. Auto-injector according to claim 3, characterized in that the syringe is held in an essentially tubular syringe carrier and supported at its proximal end therein, wherein the syringe carrier is slidably arranged in the lead screw tube, wherein the dog feature is arranged for engaging the syringe carrier for retraction of the syringe.

5. Auto-injector according to claim 2, characterized in that the first gear member is coupled to the retraction slider tube for joint axial translation but independent rotation.

6. Auto-injector according to claim 5, characterized in that the activating means comprises a trigger button, arranged at the distal end of the outer casing and operable by being depressed in proximal direction, wherein the trigger button is arranged to be prevented by the first gear member from being fully depressed when the skin contact trigger element is in its proximal position, wherein the trigger button is arranged to be unlocked for full depression by the first gear member when the skin contact trigger element is in its distal position.

7. Auto-injector according to claim 6, characterized in that at least one resilient beam element is proximally arranged on the trigger button, wherein a first rib is arranged in the outer case for deflecting the beam element inwards on depression of the trigger button by at least one ramp arranged on the first rib and/or on the beam element, wherein a first shoulder is arranged on a distal end of the first gear member, wherein the beam element is arranged to abut against the first shoulder when deflected and when the skin contact trigger element is in its proximal position, wherein the first shoulder is arranged to be translated in distal direction by translation of the skin contact trigger element into the distal position in a manner to allow inward deflection of the beam element proximally behind the first shoulder.

8. Auto-injector according to one of the claims 6, characterized in that a ring-shaped locking slider is arranged inside the outer casing around the follower tube and in a splined engagement with the outer casing so as to allow translation and prevent rotation, wherein in an initial state the locking slider is in a distal position splined to the follower tube so as to allow relative translation and prevent relative rotation, wherein the locking slider is arranged to be translated in proximal direction by the trigger button on full depression in a manner to disengage from the follower tube so as to allow rotation of the follower tube.

9. Auto-injector according to claim 1, characterized in that the second gear member is coupled to the stopper by a plunger which is releasably engageable with the second gear member for joint axial movement, wherein the plunger is disengageable from the second gear member upon the second gear member reaching its maximum proximal position.

10. Auto-injector according to claim 9, characterized in that the plunger is engageable with the second gear member by at least one plunger ball detent, wherein the ball detent is supported by the first gear member when engaged and wherein the plunger is disengageable by the ball detent reaching a pocket in the first gear member and the detent ball dropping into the pocket.

11. Auto-injector according to claim 9, characterized in that the plunger comprises a plunger rear and a plunger front telescoped into each other, wherein a plunger spring is arranged between the plunger rear and plunger front, wherein the plunger spring is arranged for being partially compressed when the plunger is being advanced to push the stopper towards the proximal end.

12. Auto-injector according to claim 11, characterized in that the second gear member is provided with pockets containing a respective viscous damper at the proximal end of the second gear member the viscous damper arranged for being compressed by a respective rib arranged in the proximal end of the outer casing when the second gear member nearly reaches a maximum proximal position thereby resolving part of the load from the second gear member and allowing the plunger spring to expand.

13. Auto-injector according to claim 2, characterized in that the first gear member and the retraction slider tube exhibit respective shoulders facing each other and held together by a coupling ring.

14. Auto-injector according to claim 3, characterized in that the lead screw thread has a variable pitch arranged in a manner to advance the second gear member faster and with less force when inserting the hollow needle and more slowly with increased force when expelling the medicament.

15. Auto-injector according to claim 1, characterized in that a finger guard is provided in the outer casing at the proximal end, the finger guard comprising a sheet metal spring with two inwardly biased spring arms arranged for bearing against a protective needle shield arranged at the hollow needle, the sheet metal spring further having a respective locking arm assigned to each spring arm biased in distal direction thus bearing against the respective spring arm when the protective needle shield is in place, wherein the spring arms are arranged to move inwards when the protective needle shield is removed thus allowing the locking arms to move distally into a position where they prevent the spring arms from being pushed outward again.

\* \* \* \* \*